United States Patent [19]

Dower

[11] Patent Number: 4,910,140

[45] Date of Patent: Mar. 20, 1990

[54] ELECTROPORATION OF PROKARYOTIC CELLS

[75] Inventor: William J. Dower, San Anselmo, Calif.

[73] Assignee: Bio-Rad Laboratories, Inc., Hercules, Calif.

[21] Appl. No.: 182,804

[22] Filed: Apr. 18, 1988

[51] Int. Cl.$^4$ ............................................ C12N 15/00
[52] U.S. Cl. .................................. 435/172.3; 435/173; 435/252.3; 435/320; 935/52; 935/55; 935/79; 935/84
[58] Field of Search .................. 435/173, 172.3, 252.3, 435/320; 935/52, 55, 79, 84

[56] References Cited

U.S. PATENT DOCUMENTS 4,081,340  3/1978  Zimmerman et al. ............... 204/180
4,849,355  7/1989  Wong ................................ 435/172.3

OTHER PUBLICATIONS

"Lividans by electroporation," FEMS Microbiology Letters, vol. 42, pp. 239–244 (1987).
Davis et al., Microbiology, Harper & Row: New York, pp. 34 and 878 (1968).
Shigekawa et al., "Electroporation of Eukaryotes and Prokaryotes: A General Approach to the Introduction of Macromolecules into Cells," BioTechniques, vol. 6, No. 8, pp. 742–751 (1988).
Powell et al., "A Simple and Rapid Method for Genetic Transformation of Lactic Streptococci by Electroporation," Appl. Environ. Microbiol., vol. 54, No. 3, (Mar. 1988).
Miller et al., "High-voltage Electroporation of Bacteria," Proc. Nat'l Sci., vol. 85, pp. 856–860 (Feb. 1988).
BioRad Laboratories, "Gene Pulser TM Transfection Apparatus Operating Instructions and Applications Guide," pp. 1–29.
MacNeil, "Introduction of Plasmid DNA into Streptomyces".
Alberts et al., Molecular Biology of the Cell, p. 923 (1983).
Gene Pulser Transformation Apparatus . . . Guide, Bio-Rad Labs. 1–29.
Chassy et al. (1987) FEMS Microbiol. Lett. 44:173–177.
Powell et al. (1988) Appl. Environ. Micriobiol. 54:655–660.
Harlander (1987) Streptococcal Genetics, pp. 229–233.
Potter et al. (1984) Proc. Natl. Acad. Sci. U.S.A. 81:7161–7165.
Zeitschrift Fur Allgemeine Mikro. (1983) 23:595.
Miller et al. (1988) Proc. Natl. Acad. Sci. U.S.A. 85:856–860.
Dower (1987) Molecular Biology Reports 1:5.

Primary Examiner—John F. Niebling
Assistant Examiner—Isabelle Rodriguez
Attorney, Agent, or Firm—Townsend and Townsend

[57] ABSTRACT

Electroporation of prokaryotic cells is achieved by the application of high-intensity electric fields of short duration to reversibly permeabilize the cell walls. Preferably, the field strength of the applied will be at least about 5 kV/cm and the duration of the exposure will be in the range from 2 to 20 msec. Macromolecules may be introduced to the cells or obtained from the cells during this period of cell wall permeability. Most commonly, the method will be utilized for transformation of the cells with nucleic acids. Very high transformation efficiencies in the range from $10^9$ to $10^{10}$ cells/µg and transformation frequencies approaching 80% and above have been achieved.

14 Claims, 4 Drawing Sheets

ELECTROPORATION OF PROKARYOTIC CELLS

BACKGROUND OF THE INVENTION

1. Field of the Invention

The present invention relates generally to the permeabilization of prokaryotic cell walls by electroporation. More particularly, the invention relates to a method and system for the electroporation-enhanced transformation of prokaryotic cells with nucleic acids.

Electroporation has heretofore been employed to assist in the transfection of eukaryotic cells, including intact animal cells and plant protoplasts, both of which are substantially free from rigid cell walls. The cells to be transformed are suspended in a solution between a pair of electrodes, and an electrical pulse is supplied which has the effect of increasing the permeability of the cell membrane to the passage of nucleic acids and other substances. The field strength employed in the electroporation of eukaryotic cells has typically been in the range from about 0.5 to 1 kV/cm.

Electroporation has been used only to a very limited extent in the transformation of prokaryotic cells. The rigid cell wall of prokaryotic cells appears to be generally refractory to the passage of nucleic acids under the conditions of electroporation which have been utilized with eukaryotic cells. Electroporation of prokaryotes has generally been successful only after the rigid cell wall has been at least partially digested.

At present, chemical treatment is the method of choice for promoting transformation of prokaryotic cells by the uptake of exogenous nucleic acids. Such chemical treatment, however, varies widely in effectiveness among different types of prokaryotes. Even with the most amenable bacterial hosts, e.g., E. coli, the efficiency of transformation achieved using chemical treatment methods seldom exceeds about $10^8$ transformants/μg of nucleic acids and is frequently much less. Moreover, the chemical treatment methods often require lengthy regeneration periods for the treated hosts and do not always achieve consistent results.

For these reasons, it would be desirable to provide methods and systems for performing electroporation of prokaryotic cells, where said methods and systems are capable of inducing permeability of the rigid cell wall. It would be particularly desirable if such methods were effective with most or all types of prokaryotic cells and were capable of providing a very high efficiency of transformation.

2. Description of the Background Art

A method for the electroporation-assisted transformation of E. coli is described in a brochure entitled "Gene Pulser TM Transformation Apparatus Operating Instructions and Applications Guide," distributed by Bio-Rad Laboratories, Inc., Richmond, Calif. 94804. The method employs a cell suspension volume of 0.8 ml and discloses a maximum transformation efficiency of $10^6$ cells/μg DNA. Following the instructions in the Bio-Rad Applications Guide, transformation of Lactobacillus casei (Chassy and FLickinger (1987) FEMS Microbiology Lett. 44: 173–177) and *Streptococcus lactis* (Powell et al. (1988) Appl. Environ. Microbiol. 54: 655–660) have also been achieved. Harlander (1987) "Transformation of Streptococcus lactis by Electroporation," in *Streptococcal Genetics*, Freti and Curtis, eds., pp 229–233, describes the electroporation of intact *S. lactis*, where the cells are subjected to very short (5 μsec) electric pulses of up to 11.6 kV/cm while being centrifuged in a sucrose density gradient. U.S. Pat. No. 4,081,340, describes a method for increasing the permeability of the skin of cells by applying a constant electric field to a flowing suspension of cells. Potter et al. (1984) Proc. Natl. Acad. Sci. USA 81: 7161–7165 describes an electroporation cell having opposed electrodes spaced by 0.5 cm and used to transfect mouse lymphocytes and fibroblasts. Although reference is made to the transformation of E. coli cells, no conditions are disclosed for achieving such transformation. Zeitschrift Fur Allgemeine Mikrobiologie (1983) 23: 595 describes the electroporation of polyethylene glycol-treated Bacillus protoplasts which resulted in an increased rate of transformation. Miller et al. (1988) Proc. Natl. Acad. Sci. USA 85: 856–860 describes the method of the present invention applied to the transformation of *Campylobacter jejuni*.

SUMMARY OF THE INVENTION

The present invention provides methods and apparatus for the electroporation of prokaryotic cells. Such electroporation renders the rigid prokaryotic cell wall permeable to macromolecules, such as nucleic acids, facilitating their passage between the extracellular and intracellular environment. In particular, the present invention is useful for transforming prokaryotic cells with exogenous nucleic acids at very high efficiencies, frequently in the range from about $10^9$ to $10^{10}$ transformants/μg nucleic acid and above, and very high transformation frequencies, often as high as 80% and under appropriate conditions, approaching 100%. Such transformation can be achieved without the need to chemically treat the cells to induce cell wall permeability.

The apparatus includes a sample cuvette having a pair of opposed, closely spaced-apart electrodes which define a sample holding region therebetween. A suspension of the cells to be electroporated is held in the sample holding region, and the electrodes are connected to a pulse generator capable of providing a short duration pulse having an electrical field strength of at least about 5 kV/cm, usually being at least about 10 kV/cm, and preferably being up to about 15 kV/cm. To promote such high field strengths, the spacing between the electrodes will be less than about 2.5 mm, usually being in the range from about 0.5 mm to 2.5 mm, and preferably being in the range from about 1.0 mm to 2.0 mm.

The volume of sample in the holding region may vary widely, being limited at the upper end only by the available electrode area. The sample volume will typically be in the range from about 1 μL to 1 ml, preferably being in the range from about 5 μL to 200 μL, and more preferably being in the range from 10 μL to 100 μL. A small sample volume below about 100 μL is beneficial in several ways. First, a reduced sample size between the electrodes will provide a higher electrical impedance which allows operation at a reduced current for a fixed voltage or electric field strength. Second, the reduced volume increases the nucleic acid concentration obtained from an available amount of nucleic acid, which in turn has been found to substantially enhance the transformation frequency. Thus, the number of transformants obtained from a fixed amount of nucleic acid can be increased by reducing the sample volume of the cell suspension subjected to electroporation. Transformation frequencies of 80% and above may be obtained with nucleic acid concentrations of at least about 7.5 μg/ml.

The method of the present invention comprises introducing prokaryotic cells suspended in a low electrical conductivity solution to the sample holding region between the electrodes at a high density, typically in the range from about $10^9$ to $10^{11}$ cells/ml, preferably in the range from about $10^{10}$ to $5 \times 10^{10}$ cells/ml. An electric pulse having a field strength in the range from about 5 to 15 kV/cm or above, is then applied across the electrodes to permeabilize the cell wall and promote the transfer of macromolecules and other substances across the cell wall. Conveniently, the electrical pulse will have an exponential decay waveform provided by the discharge of a capacitor. Other waveforms, such as square waves, having the suitable field strength and duration are also suitable. Pulses having an exponential waveform will usually have a decay time constant $\tau$ in the range from about 2 to 20 msec or longer, depending on the field strength and the cell type being treated. After exposure to the electrical pulse, the cells are preferably transferred substantially immediately to a suitable growth medium. It has been found that such rapid transfer greatly enhances the observed transformation efficiency and cell viability.

The method of the present invention has been found to allow for the selection of transformants without reliance on a selectable marker. Previous transformation techniques, including electroporation-assisted transformation, have yielded transformation frequencies which are so low that it is necessary to introduce a detectable marker, typically antibiotic resistance, together with the desired nucleic acids. Transformed colonies may then be selected based on the presence of the marker, typically by growing the colonies on a selective media, e.g., one containing the antibiotic to which resistance has been introduced in the transformants. With the very high transformation frequencies achievable with the present invention, it is no longer necessary to relay on such detectable markers. Transformant colonies will be predominant, approaching 100% in some cases.

DESCRIPTION OF THE SPECIFIC EMBODIMENTS

According to the present invention, prokaryotic cells having cell walls which are normally refractory to the passage of macromolecules are treated to enhance their permeability. The cells are subjected to an electric field under particular conditions which render the cell wall permeable to such macromolecules. In particular, it has been found that very efficient uptake of macromolecules, such as nucleic acids, may be achieved by subjecting the prokaryotic cells to a high intensity, short duration electrical field while in the presence of the macromolecule. Such high uptake efficiencies are further enhanced by transferring the cells to a suitable growth medium substantially immediately after their exposure to the electric field.

The present invention is effective with a wide variety of prokaryotic cells, including both gram-positive and gram-negative bacterial cells. In general, bacterial cells include a cytoplasmic membrane surrounded by a rigid cell wall. Gram-positive bacteria have a cell wall composed of a single, dense peptidoglycan layer surrounding the membrane, while gram-negative bacterial have a cell wall including a thin peptidoglycan layer surrounded by an outer membrane.

Gram-positive bacteria susceptible to electroporation by the methods of the present invention include Micrococcaceae, such as Staphylococcus, Micrococcus, and Sarcina; Streptococcaceae, such as Streptococcus and Leuconostoc; Lactobacillaceae, such as Lactobacillus; Propionibacteriaceae, such as propionibacterium, Corynebacterium, Listeria, and Erysipelothrix; and Bacillaceae, such as Bacillus and Clostridium. Suitable gram-negative bacteria include Enterobacteriaceae, such as Escherichia, Erwinia, Shigella, Salmonella, Proteus, and Yersinia; Brucellaceae, such as Brucella, Bordetella, Pasteurella, and Hemophilus; Azobacteraceae, such as Azotobacter; Rhizobiaceae, such as Rhizobium; Nitrobacteriaceae, such as Nitrosomonas, Nitrobacter, and Thiobacillus; Pseudomonadaceae, such as Pseudomonas and Acetobacter; Spirillaceae, such as Photobacterium, Zymonomas, Aermonas, Vibrio, Desulfovibrio, and Spirillum; and Actinomycetales, such as Mycobacterium, Actinomyces, Norcardia, and Streptomyces.

The present invention will be useful with bacteria which have previously been recognized as suitable hosts for receiving exogenous nucleic acids, particularly DNA plasmids. Such cloning hosts include *E. coli*, Pseudomonas species, including fluorocens and putida, *Bacillus subtillis*, and the like. The method will also be useful for introducing exogenous nucleic acids to bacterial hosts which have heretofore been refractory to chemical transformation of intact cells. Such hosts include *Campylobacter jejuni, Haemophilus pleuropneumoniae, Bortedella pertussis*, certain strains of *Cyanobacteria, Listeria monocytogenes, Myxococcus xanthus*, and *Rhizobium meliloti*, and the like.

Useful bacterial cultures may be obtained from numerous sources, including culture collections such as the American Type Culture Collection, Rockville, Md. 20852, and various commercial suppliers. Alternatively, they may be isolated from natural habitats. Once obtained, the bacterial cultures may be maintained in a viable state or may be frozen or lyophilized until needed.

Prior to treatment according to the present invention, the bacterial cultures will be grown out to a preselected density where the cells are still rapidly dividing, usually in the range from about $10^7$ to $5 \times 10^8$ cells/ml, and then harvested, typically by centrifugation or filtration. The collection of rapidly growing cells has been found to substantially contribute to the achievement of high transformation efficiencies. The harvested cells will be washed, using either water or a low conductivity medium, in order to reduce the concentration of salts and electrical conductivity of the suspension solution. Usually, the cells will be washed, resuspended in water or low conductivity medium, and collected by centrifugation or filtration, one or more additional times until a suspension having a desired concentration and electrical conductivity, as discussed in greater detail hereinbelow, is obtained. As the cells are no longer in a suitable growth medium, they should either be used within several hours or frozen in a suitable cryoprotectant prior to treatment by the method of the present invention.

The final cell density, after washing and concentration, will usually be in the range from about $5 \times 10^9$ to $5 \times 10^{10}$ cells/ml, with the upper limit corresponding to the highest cell density achievable with the type of cell being treated. The final salt concentration and the nature of the suspension fluid should be selected to provide as high an electrical resistance in the sample volume as obtainable for the cell suspension, typically above about $1000\Omega$, preferably being above about $5000\Omega$. Conveniently, a non-conductive medium, such as water or sucrose, will be used for suspending the cells.

The method of the present invention may be used to either introduce substances into the bacterial cells, or to collect intracellular substances released from the cells into the extracellular environment. Although nucleic acids and other macromolecules will be the most common form of substance to be introduced to the bacterial cells, other small molecules, including drugs, dyes, labelled precursors, such as labelled nucleotides and amino acids, and the like, may also be introduced. Exemplary macromolecules to be introduced (in addition to nucleic acids) include proteins, such as enzymes, antibodies, hormones; carbohydrates; and the like. Intracellular substances may also be collected after passing through the cell wall made permeable by the method of the present invention. In particular, nucleic acids, proteins, and other macromolecules which are being over-produced by the cell may be released into the suspension medium to facilitate their collection.

The nucleic acids being introduced to the bacterial cells include both DNA and RNA, and may be in either a linear or circular form. Conveniently, plasmid DNA including an origin of replication recognized by the desired bacterial host may be employed when available. For example, pBR322 may be introduced to an *E. coli* host where it will be capable of stable replication. Similarly, plasmids pUB110 and pC194 may be introduced to *Bacillus subtillis* hosts where they are capable of stable replication. Other plasmids suitable for a wide variety of hosts are available and well described in the scientific and patent literature.

The nucleic acids may or may not include a selectable marker, such as antibiotic resistance, heavy metal resistance, or the like. Such markers allow for the selection of transformants based on the phenotypic characteristic conferred by the marker. Most commonly, antibiotic resistance allows for selection of transformants on a selective media containing the antibiotic. Cells which are transformed with the marker survive on the media and form transformed colonies. Cells which have not been transformed will die as a result of the antibiotic. Such markers may be introduced as a part of the nucleic acids or may be separately introduced by co-transformation.

The present invention enjoys the advantage that use of selectable markers is not required. Because of the very high transformation frequencies achievable, often as high as 80% and under appropriate conditions approaching 100%, transformation may be carried out with the introduction of a selectable marker. The percentage of colonies grown out, however, will be the same as the transformation frequency. Thus, most colonies will be transformed and transformation can be confirmed based on some phenotype conferred by the nucleic acids, such production of a particular protein or other observable characteristic.

The method is particularly useful in cloning uncharacterized nucleic acids, for example uncharacterized plasmids obtained from various bacterial strains. Such plasmids may be isolated by gel electrophoresis from a bacterial strain which has not been well characterized. Using the electroporation method of the present invention, the isolated plasmid may then be introduced to a well characterized strain of the same bacteria and the phenotypic characteristics conferred by the plasmid observed.

The apparatus of the present invention includes a pulse generator capable of producing an electrical pulse having desired characteristics and a sample cuvette which contains the prokaryotic cell suspension while it is being subjected to the pulse provided by the pulse generator. The sample cuvette includes a pair of opposed, electrodes which define a sample holding region. Conveniently, the electrodes will usually be planar and spaced-apart by a uniform distance, although non-planar electrodes, such as concentric, and non-uniform spacing may also find use. The specific construction of the sample cuvette is not critical, although it will usually be composed of a non-electrically conductive material, such as plastic, glass, ceramic, or the like.

The electrodes will be composed of an electrically conductive material, typically a metal or carbon. Suitable electrode materials include aluminum, silver, gold, alloys thereof, and the like.

The electrodes will typically be in the form of metal strips having dimensions so that the electrode area available to be exposed to the liquid cell suspension will be in the range from about 5 mm$^2$ to 10 cm$^2$, typically being in the range from about 10 mm$^2$ to 2 cm$^2$. The actual electrode area exposed, of course, will depend on the volume of the cell suspension introduced to the sample holding region. Normally, the actual volume will be minimized to enhance the transformation frequency, as demonstrated in the Experimental section below.

The interelectrode spacing will be below about 2.5 mm, usually being in the range from about 0.5 mm to 2.5 mm, and preferably being in the range from 1.0 mm to 2.0 mm. The interelectrode spacing is critical in that it determines the electric field strength to which the sample is exposed. Generally, it is desirable to minimize the electrode spacing in order to maximize the electric field strength for a particular voltage produced by the pulse generator. Spacing below about 0.5 mm, however, is generally not suitable as it increases the likelihood of arcing between the electrodes at the field strengths of interest increases the transformation frequency.

Figure 1:
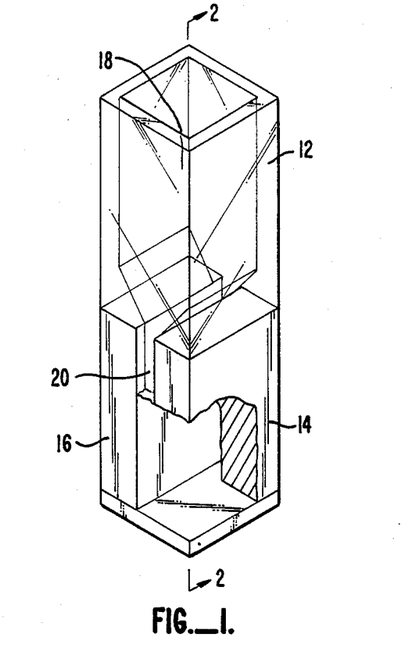
FIG. 1 is a sample cuvette constructed in accordance with the principles of the present invention shown in perspective with portions broken away.
Figure 2:
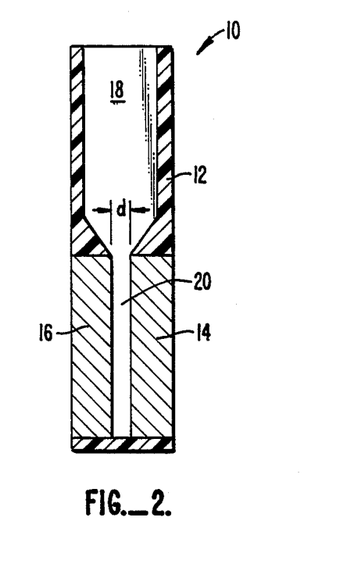
FIG. 2 is a cross-sectional view of the sample cuvette taken along line 2—2 in FIG. 1.

Referring to FIGS. 1 and 2, an exemplary sample cuvette 10 suitable for use in the method of the present invention is illustrated. The cuvette 10 includes a non-electrically conductive shell 12 having opposed aluminum electrodes 14 and 16 at its lower end. The shell 12 defines an upper chamber 18 capable of receiving a pipette or other device for transferring a prokaryotic cell suspension to a sample holding region 20 defined between the electrode 14 and 16. The interelectrode distance d is 0.2 cm and the available electrode area (for each electrode) is 2 cm$^2$. The maximum volume of the sample holding region 20 is thus 0.4 ml, although much smaller volumes (typically about 40 μL) will be employed. The dimensions of the sample cuvette 10, of course, may vary within the ranges set forth above without departing from the present invention.

Figures 3, 4:
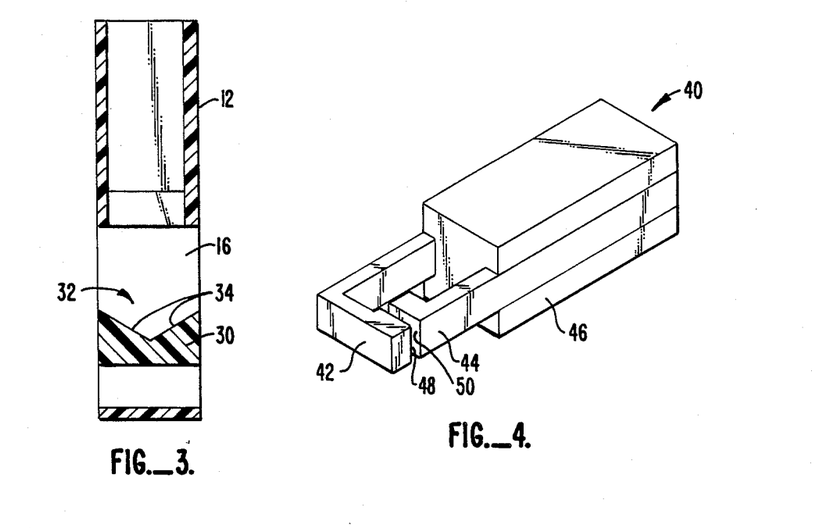
FIG. 3 is a cross-sectional view of a sample cuvette including an insert to define a low volume pocket between opposed electrodes.
FIG. 4 illustrates an alternative construction of a sample cuvette where the sample is maintained between opposed electrodes by capillary forces.

Referring now to FIG. 3, a low volume modification of the sample cuvette 10 of FIGS. 1 and 2 will be described. An insert 30 is placed between electrodes 14 and 16 and defines a pocket 32 having inclined walls 34. The pocket 32 has a depth at its lowest point of about 4 mm and thus has a total volume of about 20 μL and is suitable for sample volumes in the range from about 5 to 15 μL.

A third embodiment 40 of the sample cuvette of the present invention is illustrated in FIG. 4. The cuvette 40 includes a pair of electrodes 42 and 44 mounted in a non-electrically conductive base 46. Electrode 42 inlcudes an exposed face 48 which is parallel to and spaced-apart from exposed face 50 of electrode 44. The gap between the electrode faces 48 and 50 will be in the range between 0.5 mm and 2.5 mm, as set forth above, and will be capable of holding sample volumes in the range from about 5 μL to 75 μL which are held in place by capillary forces.

The pulse generator for the electroporation apparatus should be capable of providing an electric field strength of at least about 5 kV/cm in the sample holding volume, usually providing field strength of at least 10 kV/cm, and preferably being capable of providing electric field strength of 15 kV and above. The electric field strength, of course, depends on the interelectrode spacing, with a shorter interelectrode spacing resulting in a higher field strength for a fixed voltage applied across the electrodes. For the preferred interelectrode spacing of 2.0 mm, a pulse generator voltage of 1 kV will provide a maximum field strength of 5 kV/cm, while a voltage of 2.5 kV volts will provide a maximum field strength of 12.5 kV. Preferably, for the exemplary sample holder described above, the pulse generator will provide a voltage of at least about 2.5 kV and a current of at least about 125 amps.

The precise electric field strength applied to a particular type of bacteria will depend primarily on the cellular dimensions. For smaller bacteria sized from 1 to 2 μm, a higher field strength in the range from 10 to 15 kV/cm is preferred. For larger bacteria sized from 3 to 5 μm, a lower field strength in the range from 5 to 10 kV/cm is suitable. In all cases, however, a lower field strength may be at least partly compensated by a longer duration pulse.

The type of pulse waveform provided by the pulse generator is not critical. Typically, the waveform will be either an exponential decay (provided by capacitive discharge) or a square wave provided by a square wave generator. Because of the voltage and current requirements, a capacitive-discharge pulse generator will normally be preferred. The pulse generator should include adequate user safeguards to prevent shorting and excess discharge during use. A suitable pulse generator is described in copending application Ser. No. 06/872,060 filed on June 6, 1986, the disclosure of which is incorporated herein by reference.

Using the apparatus just described, the method of the present may be performed as follows. A small volume of the high density cell suspension described hereinabove is introduced to the sample holding region of the sample cuvette so that the volume is contained substantially entirely between the electrodes. Typically, the total volume of the cell suspension will be in the range from about 5 to 400 μL, more typically being in the range from about 10 to 100 μL, and preferably being below about 50 μL. The cell suspension will normally be chilled to promote permeability, typically below about 10° C., and preferably in the range from about 0 to 4° C.

To promote the permeability of the cell wall, a high-intensity electric field of short duration is applied across the electrodes. The voltage of the discharge will be selected to provide the desired electric field strength (as described above), and the duration of the discharge selected to be sufficient to result in the desired permeability. The precise voltage and pulse duration selected will depend on the nature of prokaryotic cells being treated, with higher voltages and/or longer pulse durations being utilized with more recalcitrant cell types. The pulse duration will generally be in the range from 2 to 20 msec or longer, usually being in the range from 3 to 10 msec. For square waves, the pulse duration is simply the width of the square wave applied. For an exponential decaying pulse, the pulse duration will be the time constant $\tau$, where $\tau$ equals the product of the circuit capacitance and resistance. Normally, the pulse will consist of a single pulse comprising the entire desired time period. Alternatively, the pulse may consist of a plurality of shorter pulses having a cumulative time period coming with the desired 2 to 20 msec range. Such a series of pulses must be spaced sufficiently close to one another however, so that the combined effect results in permeabilization of the cell wall, typically being spaced-apart by 5 msec or less, more preferably being spaced-apart by 2 msec or less.

For transformation, the nucleic acids will usually be present in the suspension solution during the application of the electric pulse. Unlike eukaryotic cells whose membranes frequently remain permeable for some time after exposure to the electrical pulse, the cell walls of at least many prokaryotic species display only a very limited period of permeability. Although it may sometimes be effective to introduce the nucleic acids within a short time period after exposure to the electrical pulse, usually within 30 seconds, it will generally be preferable to apply the electric pulse while the nucleic acids are present in the suspension solution.

To maximize transformation frequency, it is necessary to employ a very high nucleic acid concentration preferably being above about 5 μg/ml, more preferably being 20 μg/ml or above. Using the highest nucleic acid concentrations, transformation frequencies of 80% and above may be achieved. The present invention, however, will function with a much broader range of nucleic acid concentrations, generally from 1 pg/ml to 10 μg/ml. The transformation frequency, however, will be reduced in proportion to the reduction of nucleic acid concentration.

By performing the method of the present invention with both elevated cell concentrations and elevated nucleic acid concentrations, the yield of transformants from a given amount of nucleic acid starting material amount may be achieved. Thus, it will normally be desirable to minimize the volume of the sample holding region, which results in most efficient use of both the cells and the nucleic acids. The transformation efficiency, of course, should also be maximized by proper selection of the field strength and the duration of the electrical pulse to which the cells are exposed.

In order to further enhance transformation efficiency, the cell suspension should be removed from the sample holder substantially immediately after exposure to the electrical pulse, usually being within 60 seconds of such exposure, and preferably being within 30 seconds of such exposure. The cells should be transferred to a suitable growth media, and should be allowed to recover through a preselected period, usually equal to at least two cell doubling periods, before being further manipulated, such as being exposed to a selective media.

The following examples are offered by way of illustration, not by way of limitation.

EXPERIMENTAL MATERIALS AND METHODS

1. Cells

E. coli strains LE392 and DH5α were grown in L-broth (10 gm Bacto tryptone, 5 gm Bacto yeast extract, 5 gm NaCl per liter) with vigorous shaking at 37° C. to an $Abs_{600}$ of 0.5 to 1. The cells were harvested by chilling the flasks briefly on ice and centrifuging at $4000 \times g_{max}$ for 15 min. at 4° C. The ionic strength of the cell suspension was reduced by extensive washing. The cells from a 1 L culture were resuspended in 1 L of either cold 1 mM hepes, pH 7, or water, centrifuged as above, resuspended in 0.5 L of cold 1 mM hepes or water, centrifuged, resuspended in 20 ml of 10% glycerol, centrifuged, and finally resuspended in from 3 to 20 ml of 10% glycerol (a 50 to 300-fold concentration from the culture, depending on the experiment). This concentrated suspension was distributed in small aliquots, frozen on dry ice, and stored at −70° C.

2. DNA pUC 18 and pBR329 were prepared by alkaline lysis and doubling banding in CsCl. These preparations were about 90% supercoiled and 10% relaxed circles. The plasmids were resuspended in TE (10 mM Tris-Cl pH 8.0, 1 mM EDTA) and stored in aliquots frozen at −20° C. The DNA concentration was measured in two ways. First, the $Abs_{260}$ was measured and the concentration calculated assuming a molar extinction coefficient of $1.3 \times 10^4$ L $mol^{-1}$ $cm^{-1}$ ($1OD_{260} = 50$ μg/ml). Agarose gel electrophoresis showed no contaminating, ethidium bromide-staining material that might contribute to the absorbance readings. Second, the plsmid DNA was linearized by restriction digestion, and the band intensity on an ethidium bromide-stained agarose gel was compared with several other linear DNA species of known mass. These two methods were in agreement.

3. Chemical transformation

For comparison, competent DH5a cells were obtained from Bethesda Research Laboratories, Gaithersburg, Md. 20877, and transformed exactly according to the instructions of the supplier.

4. Electronics and electrodes

Figure 5:
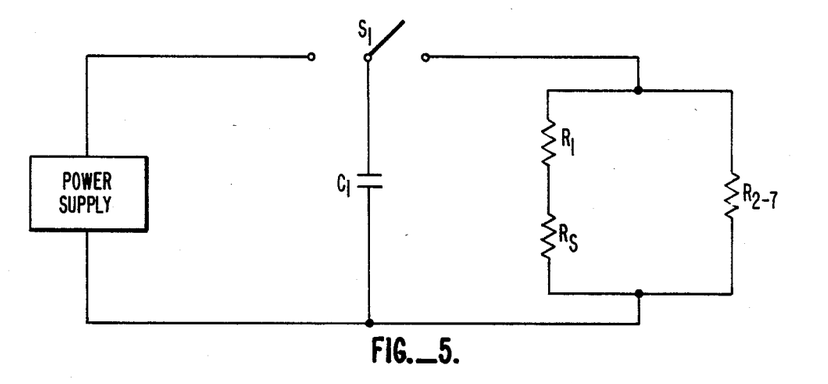
FIG. 5 illustrates electric circuitry useful for driving the electroporation cell of the present invention.

The exponential decay pulses were generated by a Gene Pulser™ Apparatus (Bio-Rad Laboratories, Richmond, Calif. 94804), set at 3 or 25 μF and from 0.2 to 2.5 kV. The output of the pulse generator was directed through a Pulse Controller Unit (Bio-Rad) containing a high power, 20Ω resistor in series with the sample, and a selection of resistors from 100 to 1000Ω in parallel with the sample. The combination of the Gene Pulser# Apparatus and Pulse Controller Unit is schematically illustrated in FIG. 5, where $R_s$ is the sample cuvette, $R_1$ is the 20Ω resistor, and $R_{2-7}$ represent the parallel resistor bank. The units are operated by first charging capacitor $C_1$ (3 or 25 μF) by throwing switch $S_1$, to the power supply. The capacitor is then discharged across the cuvette $R_s$ by throwing switch $S_1$ to the opposite pole. The resistance $R_{2-7}$ placed in parallel with the electrodes is much lower than that of the sample and determines the time constant τ of the pulse. For example, 200Ω with the 25 μF capacitor gives a 5 msec time constant. Electrode gaps of either 0.15 cm with a sample holder of the type of FIG. 4 or 0.20 cm with a sample cuvette of the type of FIGS. 1 and 2 were used. Peak field strengths of up to 16.7 kV/cm were obtained with these arrangements. Sample volumes from 35 to 40 μl were treated in the smaller sample holder, while larger volumes from 40 to 400 μl were treated on the larger cuvette.

5. Transformation protocol

The concentrated cells were thawed at room temperature, and placed on ice. 40 μl of cells were transferred to a cold, 1.5 ml polypropylene tube. 1 to 2 μl of DNA solution (in a low ionic strength TE medium was added to give a final concentration of from 10 pg/ml to 7.5 μg/ml, and the suspension mixed vigorously by flicking the tube. The cell/DNA mixture was placed between the chilled electrodes, the electrode assembly or cuvette placed in the safety chamber, and the pulse applied. Following the pulse, the cells were removed from the electrodes and mixed into 50 volumes of SOC outgrowth medium (2% Bactotryptone, 0.5% Bacto yeast extract, 10 mM NaCl, 2.5 mM KCl, 10 mM $MgCl_2$, 10 mM $MgSO_4$, 20 mM glucose) in a 17×100 mm polypropylene tube. The samples were incubated, with shaking at 225 rpm, for 1 hour at 37° C. At the end of this expression period, the cells were diluted appropriately in SOC and plated on L-agar containing either ampicillin (100 μg/ml), tetracycline (10 μg/ml), or chloramphenicol (34 μg/ml) to screen for transformants. Transformation efficiency was calculated as CFU/μg of plasmid DNA applied. Dilutions were plated on non-selected L-agar to assess cell survival.

RESULTS

1. Electrical variables

The pulses used were of exponential decay waveform generated by the discharge of a capacitor C (see FIG. 5). These pulses have a peak voltage ($V_o$) and a time constant (τ), where the time constant is determined by the following formula:

τ = RC, where
  τ = time required for voltage to decline to $V_o/e$ (sec) which equals RC;
  R = total resistance across the capacitor (Ω);
  C = capacitance of capacitor (Farads); and
  $V_o$ = peak voltage (volts).

The voltage effect experienced by the cells depends on the field strength, $E_o = V_o/d$, where d is the distance between the electrodes. The current, power, charge, and energy applied to the sample depends on the voltage ($V_o$), resistance (R), and capacitance (C) of the pulse generator.

2. Effect of field strength on transformation

Figure 6:
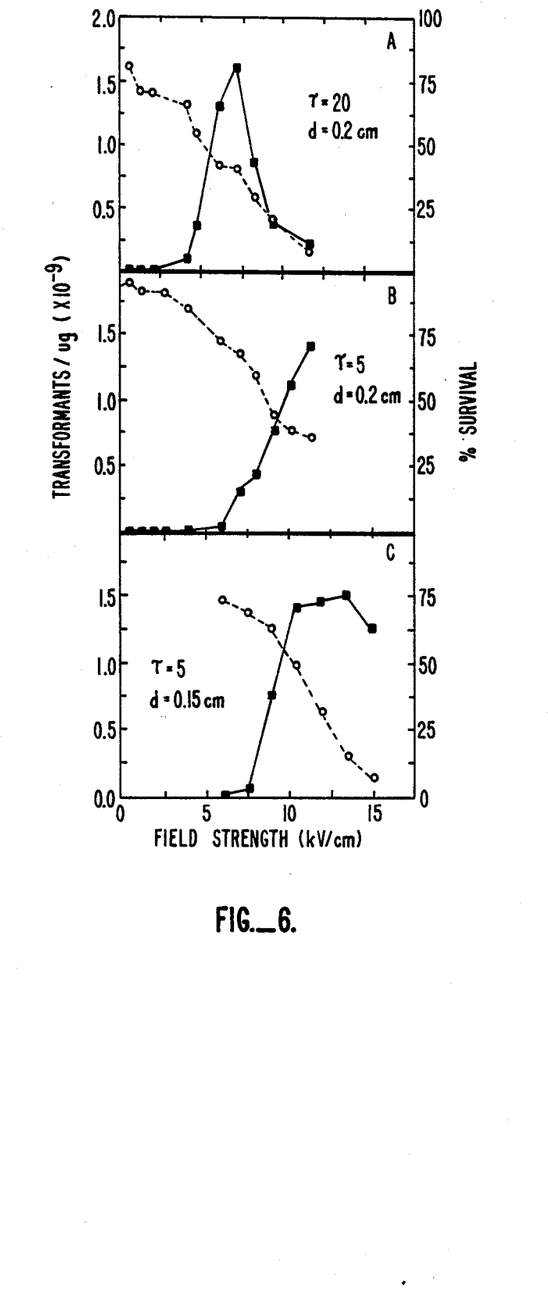
FIGS. 6–9 are graphs illustrating results as described in the Experimental section hereinafter.

The viability and transformability of the cells is very sensitive to the initial electric field strength of the pulses. The effectiveness of pulses with a wide range of field strengths and two time constants were compared, and the results are shown in FIG. 6. With pulses of 20 msec (panel A), peak transformation occurs at a field of about 7 kV/cm; with shorter pulses of 5 msec (panel B and C), fields greater than 11 kV/cm are required to obtain maximum transformation. Pulses of either 7 kV/cm and 20 msec or 11 kV/cm and 5 msec produce about the same level of transformation. Cell survival declines steadily with increasing field strength; and in each case shown, the maximum transformation efficiency is reached when 30 to 40% of the cells survive the pulse.

3. Effect of pulse length

Figure 7:
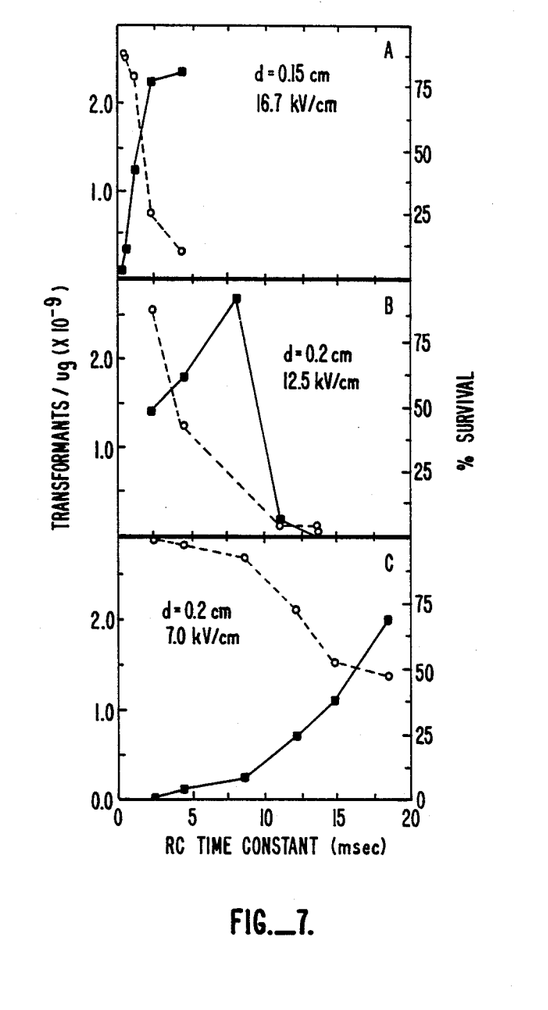

As shown in FIG. 7, the length of the pulse also has an effect on transformation efficiency, although the effect is less dramatic than that of the initial electric field strength. Time constants from 0.4 to 18 msec were obtained by changing the size of the capacitor and the resistance ($R_{2-7}$) in parallel with the sample (FIG. 5). The resistance $R_{2-7}$ is much smaller than the sample resistance and this determines the time constant obtained with any given capacitor. The experiment was performed at three field strengths, and the results are shown in FIG. 7. With the strongest electrical field of 16.7 kV/cm (panel A), pulses as short as 2.3 msec produced high levels of transformation. With weaker fields (panels B and C), the pulses must be considerably longer to obtain similar levels of transformation. As with the previous experiment, there was compensatory relationship between the pulse amplitude and duration, and peak transformation was found under conditions where about 30% of the cells survive. The ability to compensate for lower field strength by increasing the pulse lengths is limited, however. Under the conditions described above, but with fields of only 2.0 kV/cm and very long pulses (time constants of up to 900 msec), transformation has not been found to exceed about $10^6$ transformants/μg DNA.

4. Concentration of DNA and cells

Figure 8:
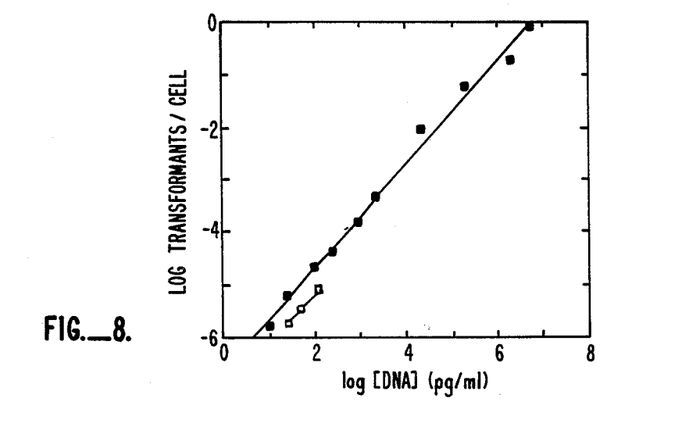

The effect of DNA concentration on transformation of *E. coli* was examined. Table 1 shows the result of pulsing the same volume of cell suspension (40 μl) with quantities of pBR329 DNA of from 0.4 pg to 0.3 μg (10 pg/ml to 7.5 μg/ml). The recovery of transformants increased linearly with DNA input (and DNA concentration) over this very wide range. Transformation efficiency at all points was about $3 \times 10^9$/μg. In contrast, varying the DNA concentration by pulsing the same mass of DNA with different volumes of cell suspension gave the same yield of transformants independently of DNA concentration. Thus, it appears that the transformation frequency (proportion of cells transformed) is related to DNA concentration. To illustrate this relationship, some of the data from Table 1 is replotted and shown in FIG. 8. The plot illustrates that under a given set of conditions, the DNA concentration determines the probability of any cell becoming transformed. Therefore at any DNA concentration, the yield of transformants should increase with the cell concentration. To confirm this hypothesis, cells at concentrations of from $1.5 \times 10^9$/ml to $2.8 \times 10^{10}$/ml were electroporated in the presence of a fixed DNA concentration. The results show a steady increase in transformants recovered over this range of cell concentration.

TABLE 1

| DNA (pg) | Vol (μl) | DNA (pg/ml) | Trans-formants | Trans/μg ($\times 10^9$) | Trans/survivor |
|---|---|---|---|---|---|
| 0.4 | 40 | 10 | $9.7 \times 10^2$ | 2.6 | $1.6 \times 10^{-6}$ |

TABLE 1-continued

| DNA (pg) | Vol (μl) | DNA (pg/ml) | Trans-formants | Trans/μg ($\times 10^9$) | Trans/survivor |
|---|---|---|---|---|---|
| 1 | 40 | 25 | $3.8 \times 10^3$ | 4.3 | $6.2 \times 10^{-6}$ |
| 4 | 40 | 100 | $1.3 \times 10^4$ | 3.6 | $2.1 \times 10^{-5}$ |
| 10 | 40 | 250 | $2.4 \times 10^4$ | 2.5 | $3.9 \times 10^{-5}$ |
| 40 | 40 | $10^3$ | $9 \times 10^4$ | 2.25 | $1.5 \times 10^{-4}$ |
| 100 | 40 | $2.5 \times 10^3$ | $2.8 \times 10^5$ | 2.8 | $4.6 \times 10^{-4}$ |
| $10^3$ | 40 | $2.5 \times 10^4$ | $5.4 \times 10^6$ | 5.4 | $9.0 \times 10^{-3}$ |
| $10^4$ | 40 | $2.5 \times 10^5$ | $3.6 \times 10^7$ | 3.6 | $6.0 \times 10^{-2}$ |
| $10^5$ | 40 | $2.5 \times 10^6$ | $1.1 \times 10^8$ | 1.2 | $1.8 \times 10^{-1}$ |
| $3 \times 10^5$ | 40 | $7.5 \times 10^6$ | $4.8 \times 10^8$ | 1.6 | $7.8 \times 10^{-1}$ |
| 4 | 40 | 100 | $2.8 \times 10^3$ | 0.7 | $9.3 \times 10^{-6}$ |
| 4 | 100 | 40 | $4.2 \times 10^3$ | 1.1 | $3.6 \times 10^{-6}$ |
| 4 | 200 | 20 | $3.4 \times 10^3$ | 0.8 | $1.8 \times 10^{-6}$ |
| 40 | 40 | 1000 | $5.5 \times 10^4$ | 1.4 | $1.8 \times 10^{-4}$ |
| 40 | 100 | 400 | $5.1 \times 10^4$ | 1.3 | $6.7 \times 10^{-5}$ |
| 40 | 200 | 200 | $5.4 \times 10^4$ | 1.4 | $3.6 \times 10^{-5}$ |

5. Effect of pre- and post-shock incubation of cells with DNA

Figure 9:
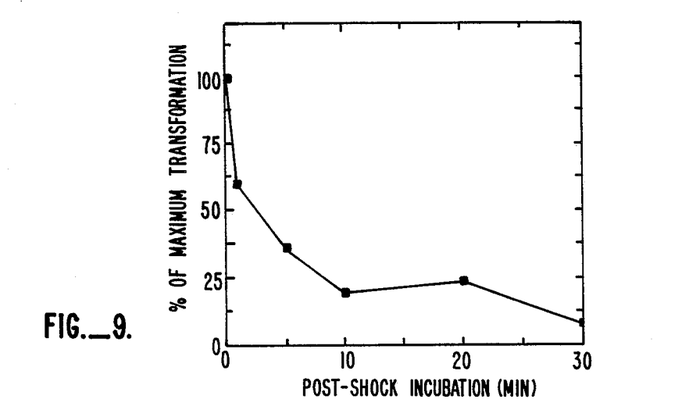

If binding of DNA to the cells is required for electroporation, increased time of incubation of DNA with the cells prior to pulsing might increase the level of transformation. Conversely, if nucleases are present in the cell suspension, increased incubation time might be detrimental for transformation. The effect of pre-shock incubation time was examined and very little difference was found over the range of 0.5 to 30 min, suggesting that a binding step may not be necessary. The effect of the time of incubation following the pulse (put preceeding the expression period) was also examined. The data in FIG. 9 show that the post-shock incubation time had a profound effect on transformation efficiency, which decreased about 3-fold in the first minute, and continued to decline by more than 20-fold in 30 min. Thus, immediate transfer (within the first minute and preferably with 30 seconds or less) of the cells after electroporation to a suitable recovery medium enhances the number of transformants obtained.

6. Comparison of transformation achieved by electroporation with chemical transformation

*E. coli* strain DH5α was transformed with pUC18 and pBR329 both by electroporation and by chemical transformation. The conditions of chemical transformation are described in Materials and Methods. The conditions of electroporation were as follows:

| | |
|---|---|
| Cell suspension volume | 40 μL |
| Cell concentration | $2.5 \times 10^{10}$ cells/ml |
| Field strength | 12.5 kV/cm |
| Time Constant (τ) | 5 msec. |

The results are set forth in Table 2, where it can be seen that the transformation efficiency achieved with electroporation is generally higher than that achieved by chemical transformation by an order of magnitude.

TABLE 2

| | DNA | Amount (pg) | Trans/μg Amp. Res. | Tet. Res.* |
|---|---|---|---|---|
| Chemical Transformation | pUC18 | 20 | $2.2 \times 10^8$ | 0 |
| | pUC18 | 50 | $2.5 \times 10^8$ | 0 |
| | pBR329 | 20 | $0.7 \times 10^8$ | $1.0 \times 10^8$ |
| | pBR329 | 50 | $0.7 \times 10^8$ | $1.0 \times 10^8$ |
| Electroporation: | pUC18 | 4 | $3.2 \times 10^9$ | 0 |
| | pUC18 | 40 | $4.1 \times 10^9$ | 0 |
| | pUC18 | 100 | $2.4 \times 10^9$ | 0 |

TABLE 2-continued

| DNA | Amount (pg) | Trans/μg Amp. Res. | Tet. Res.* |
|---|---|---|---|
| pBR329 | 4 | $0.6 \times 10^9$ | $0.5 \times 10^9$ |
| pBR329 | 40 | $1.1 \times 10^9$ | $1.0 \times 10^9$ |
| pBR329 | 100 | $1.1 \times 10^9$ | $1.0 \times 10^9$ |

*pUC18 does not express tetracycline resistance.

Although the foregoing invention has been described in some detail by way of illustration and example for purposes of clarity of understanding, it will be obvious that certain changes and modifications may be practiced within the scope of the appended claims.

What is claimed is:

1. A method for transforming bacterial cells, said method comprising:
   suspending the bacterial cells in a sample volume characterized by a low electrical conductivity solution of at least 1000Ω and a cell density of at least about $5 \times 10^9$ cells/ml while the walls of said cells remain substantially intact;
   subjecting the cells while in the solution and in the presence of nucleic acids at a concentration of at least about 1 pg/ml to an electric pulse across the sample volume, said pulse having a field strength of at least about 5 kV/cm for a time period sufficient to permeabilize the cell wall; and
   transferring the cells substantially immediately after being subjected to the electric pulse to a media capable of supporting growth of the cells.

2. A method as in claim 1, wherein the solution has a salt concentration which results in an electrical resistance of at least about 1000Ω.

3. A method as in claim 1, wherein the time period of the pulse is in the range from about 2 to 20 msec.

4. A method as in claim 1, wherein the cell suspension is chilled to a temperature below about 10° C. prior to subjecting the cells to the electrical pulse.

5. A method as in claim 1, wherein the volume of the solution is in the range from about 1 μL to 1 ml.

6. A method as in claim 1, wherein the nucleic acids are circular.

7. A method as in claim 1, wherein the nucleic acids are linear.

8. A method as in claim 1, wherein the nucleic acids include a detectable marker.

9. A method as in claim 1, wherein the nucleic acids are free from detectable markers.

10. A method as in claim 1, wherein the nucleic acids are free from antibiotic resistance genes and heavy metal resistance genes.

11. A method as in claim 1, wherein the nucleic acids are present in the solution at a concentration of at least about 5 μg/ml.

12. A method as in claim 5, wherein the volume is in the range from about 10 μL to 100 μL.

13. A method for transforming bacterial cells, said method comprising:
   suspending the bacterial cells in a sample volume characterized by a low electrical conductivity solution of at least 1000Ω and a cell density of at least about $5 \times 10^9$ cells/ml, said cells not having been chemically treated to induce cell wall permeability;
   subjecting the cell while in the solution and in the presence of nucleic acids at a concentration of at least about 1 pg/ml to an electric pulse across the sample volume, said electric pulse having a field strength of at least about 5 kV/cm for a time period sufficient to permeabilize the cell wall; and
   transferring the cells substantially immediately after being subjected to the electrical pulse to a media capable of supporting growth of the cells.

14. A method for transforming bacterial cells having a cell wall, said method comprising:
   suspending the bacterial cells in a sample volume characterized by a low electrical conductivity solution of at least 1000Ω and a cell density of at least about $5 \times 10^9$ cells/ml;
   subjecting the cells while in the solution and in the presence of nucleic acids at a concentration of at least about 1 pg/ml to an electric pulse across the sample volume, said electric pulse having a field strength of at least about 5 kV/cm for a time period sufficient to permeabilize the cell wall; and
   transferring the cells to a media capable of supporting growth of the cells within 60 seconds of exposure to the electric pulse.

* * * * *